(12) United States Patent
Möller et al.

(10) Patent No.: US 6,949,222 B1
(45) Date of Patent: Sep. 27, 2005

(54) SYSTEM FOR MONITORING AND CONTROL IN THE STERILIZATION OF AN OBJECT

(75) Inventors: Håkan Möller, Lund (SE); Lars Näslund, Furulund (SE); Anders Kristiansson, Lund (SE)

(73) Assignee: Tetra Laval Holdings & Finance SA, Pully (CH)

( * ) Notice: Subject to any disclaimer, the term of this patent is extended or adjusted under 35 U.S.C. 154(b) by 527 days.

(21) Appl. No.: 10/070,926

(22) PCT Filed: Sep. 14, 2000

(86) PCT No.: PCT/SE00/01782

§ 371 (c)(1),
(2), (4) Date: Jul. 10, 2002

(87) PCT Pub. No.: WO01/19687

PCT Pub. Date: Mar. 22, 2001

(30) Foreign Application Priority Data

Sep. 17, 1999  (SE) ..................... 9903332

(51) Int. Cl.[7] ............... B65B 55/08; A61L 2/08
(52) U.S. Cl. ............... 422/62; 422/292; 422/300; 422/22; 422/3; 422/105; 250/492.3; 250/455.11
(58) Field of Search ............... 422/3, 22, 62, 422/292, 300, 105; 250/492.3, 455.11, 453.11

(56) References Cited

U.S. PATENT DOCUMENTS

| | | | |
|---|---|---|---|
| 3,780,308 A | 12/1973 | Nablo | |
| 3,922,835 A | 12/1975 | Reil | |
| 4,104,024 A | 8/1978 | Vogele et al. | |
| 4,225,556 A | 9/1980 | Löthman et al. | |
| 4,305,000 A | 12/1981 | Cheever | |
| 4,367,412 A | 1/1983 | Cheever | |
| 5,326,542 A | 7/1994 | Sizer et al. | |
| 5,368,828 A | 11/1994 | Carlson | |
| 5,424,034 A | 6/1995 | Hilmersson | |
| 5,433,920 A | 7/1995 | Sizer et al. | |
| 5,489,783 A | 2/1996 | Kristiansson | |
| 5,569,438 A | 10/1996 | Hilmersson | |
| 5,639,432 A | 6/1997 | Carlson | |

FOREIGN PATENT DOCUMENTS

| | | | |
|---|---|---|---|
| EP | 0054016 | | 6/1982 |
| JP | 59-115222 | | 3/1984 |
| JP | 9115222 | | 7/1984 |
| JP | 4108451 | | 4/1992 |
| JP | 11137645 | | 5/1999 |
| JP | 11169438 | | 6/1999 |
| JP | 11169438 A | * | 6/1999 |
| JP | 11248895 | | 9/1999 |
| WO | 97/43915 | | 11/1997 |
| WO | WO 97/43915 | * | 11/1997 |
| WO | 98/16287 | | 4/1998 |

* cited by examiner

*Primary Examiner*—John Kim
*Assistant Examiner*—Sean E. Conley
(74) *Attorney, Agent, or Firm*—Burns, Doane, Swecker & Mathis LLP

(57) ABSTRACT

The disclosure relates to a system for monitoring and control in the sterilization of an object (1) which, for the purpose of sterilization, is electron irradiated from an electron radiation source (2) past which the object is led or conveyed. The system includes a detector (11), a converter (13), a generator (18), a process control unit (19), as well as an ejector mechanism (26) which is disposed to be activated for ejecting the sterilized object (1) on receipt of a negative comparison signal from the process control unit (19).

8 Claims, 2 Drawing Sheets

SYSTEM FOR MONITORING AND CONTROL IN THE STERILIZATION OF AN OBJECT

TECHNICAL FIELD

Figure 1:
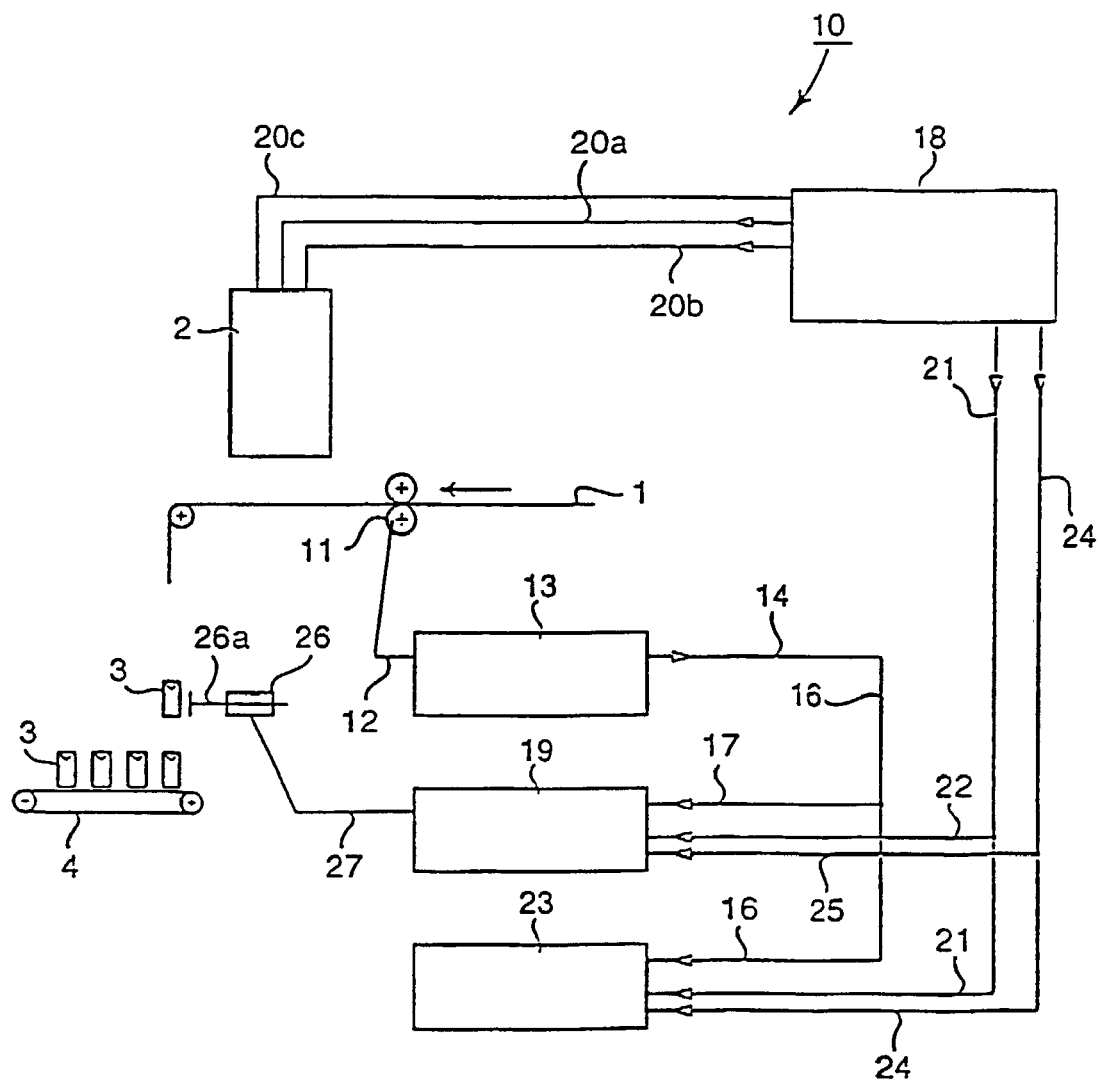

The present invention relates to a system for monitoring and control in the sterilisation of an object which, for the purpose of sterilisation, is electron irradiated from an electron radiation source past which the object is led or conveyed in order to receive the requisite radiation dose for the desired sterilisation effect. In particular, the present invention relates to such a system for the sterilisation of a planar or optionally configured packaging blank.

BACKGROUND ART

Within the packaging technology, use is often made of consumer packages of single-use disposable type for packing and transporting liquid foods. The demands placed on such so-called single-use disposable packages is that they must be easy to produce and handle and that they, moreover, impart to their packed product the requisite product protection in order to be able to store the product in an unopened package without the risk that the product deteriorate and become unfit for consumption.

The requirement on requisite product protection is, of course, particularly important when the product which is to be packed is a food, and in order to make for reliable handling of a packed food, use is therefore most generally made of so-called aseptic packages which are a special type of the above-mentioned single-use packages. An aseptic package differs from a corresponding non-aseptic package principally in that the aseptic package, prior to filling, is subjected to a bactericidal treatment (e.g. a sterilisation treatment) and that the thus treated package is thereafter filled and sealed under sterile conditions in order to reduce the risk of re-infection.

Aseptic single-use packages are produced, for example, from a web of a packaging material in that the web is, for the purpose of sterilisation, led through a bath of aqueous hydrogen peroxide solution and thereafter reformed into packages which are filled with the pertinent, separately sterilised product and sealed in a sterile filling atmosphere. The entire production cycle, including the sterilisation, is put into effect with the aid of modern, rational packaging and filling machines of the type which both form, fill and seal aseptic packages at a product output speed of several thousands of packages per hour, practically round the clock, without disruption other than for planned normal operational maintenance.

Since such high production output speeds require correspondingly extremely high web speeds, it is obvious that the contact of the web with the sterilising hydrogen peroxide bath will be only brief, unless the bath is extended to an excessive length. In order to achieve the desired sterilisation effect at these high production output speeds, it is therefore important that all parameters relevant for the sterilisation, e.g. temperature, concentration etc., are monitored and maintained at their predetermined levels throughout the entire production cycle in order to avoid unnecessary production waste because of insufficient sterilisation of the web.

In the described, prior art packaging production, the temperature and hydrogen peroxide concentration of the sterilisation bath are set initially at their respective levels for the desired sterilisation of the web at the current web speed, whereafter the temperature of the bath is continuously monitored during the sterilisation, while the concentration of the bath is only monitored at predetermined time intervals, e.g. after four or eight hours. Such an intermittent monitoring is unsatisfactory and can, in the worst case scenario, lead to all packages produced during the meantime having to be rejected (product waste) if it proves at the time of monitoring that the concentration drastically or prohibitively deviates from the predetermined concentration level.

Another drawback inherent in the prior art sterilisation method is that it requires careful and complete removal of hydrogen peroxide from the web after passage through the hydrogen peroxide bath in order to eliminate the risk that hydrogen peroxide accompanies the web and finally comes into contact with the product which is to be packed.

Efficient removal of hydrogen peroxide from the web is, as a rule, easy to achieve in such cases where the web is entirely smooth, but is more difficult if the web displays irregularities on its surface, e.g. applied opening strips etc., where the hydrogen peroxide may readily penetrate in and become inaccessible. The problem with residual quantities of hydrogen peroxide in the sterilise web is further aggravated in those cases where the web displays incision edges with exposed paper or paperboard fibre which readily absorb and conceal residual quantities of hydrogen peroxide in the fibre layer of the web.

The problem in connection with hydrogen peroxide in a packaging material which, for the purpose of sterilisation, has been in contact with an aqueous hydrogen peroxide solution is wholly obviated by another prior art sterilisation method in which the packaging material, for the purpose of sterilisation, is irradiated with emitted electrons from an electron radiation source which directs electron beams at at least those parts of the packaging material which later come into contact with a product packed in the sterilised packaging material.

A sterilisation method which employs electron irradiation instead of hydrogen peroxide as the sterilisation agent is extremely rapid and efficient in the sterilisation of packaging material and/or ready-to-fill packages, but none of the hitherto prior art electron irradiation methods has a system for the continuous monitoring and control of the sterilisation throughout the entire sterilisation process. In particular, the prior art electron irradiation methods lack a system which is capable of responding instantaneously to a detected deviation in a monitored process parameter and immediately thereafter activating a control unit for correcting the deviating parameter back to the correct level, at the same time as only that part of the packaging material which had been sterilised at the incorrect parameter level is automatically rejected without needing to stop the sterilisation process.

OBJECTS OF THE INVENTION

One object of the present invention is therefore to obviate the above-considered shortcomings and drawbacks inherent in the above-described sterilisation methods.

A further object of the present invention is to provide an efficient and reliable system for monitoring and control in the sterilisation of an object which, for the purpose of sterilisation, is electron irradiated from an electron radiation source past which the object is led or conveyed at a predetermined speed in order to receive a sufficient irradiation dose for the intended sterilisation effect.

A particular object of the present invention is to provide a system for monitoring and control in the sterilisation of a packaging material or a package by means of electron irradiation, which makes for continuous monitoring and control of the sterilisation process and the immediate rejection of incorrectly sterilised packaging material, without the sterilisation process or operation otherwise needing to be stopped.

Solution

These objects will be attained according to the present invention by means of the system defined in appended claim 1. Further advantageous details and aspects of the present invention are apparent from the appended subclaims.

BRIEF DESCRIPTION OF THE ACCOMPANYING DRAWINGS

Figure 2:
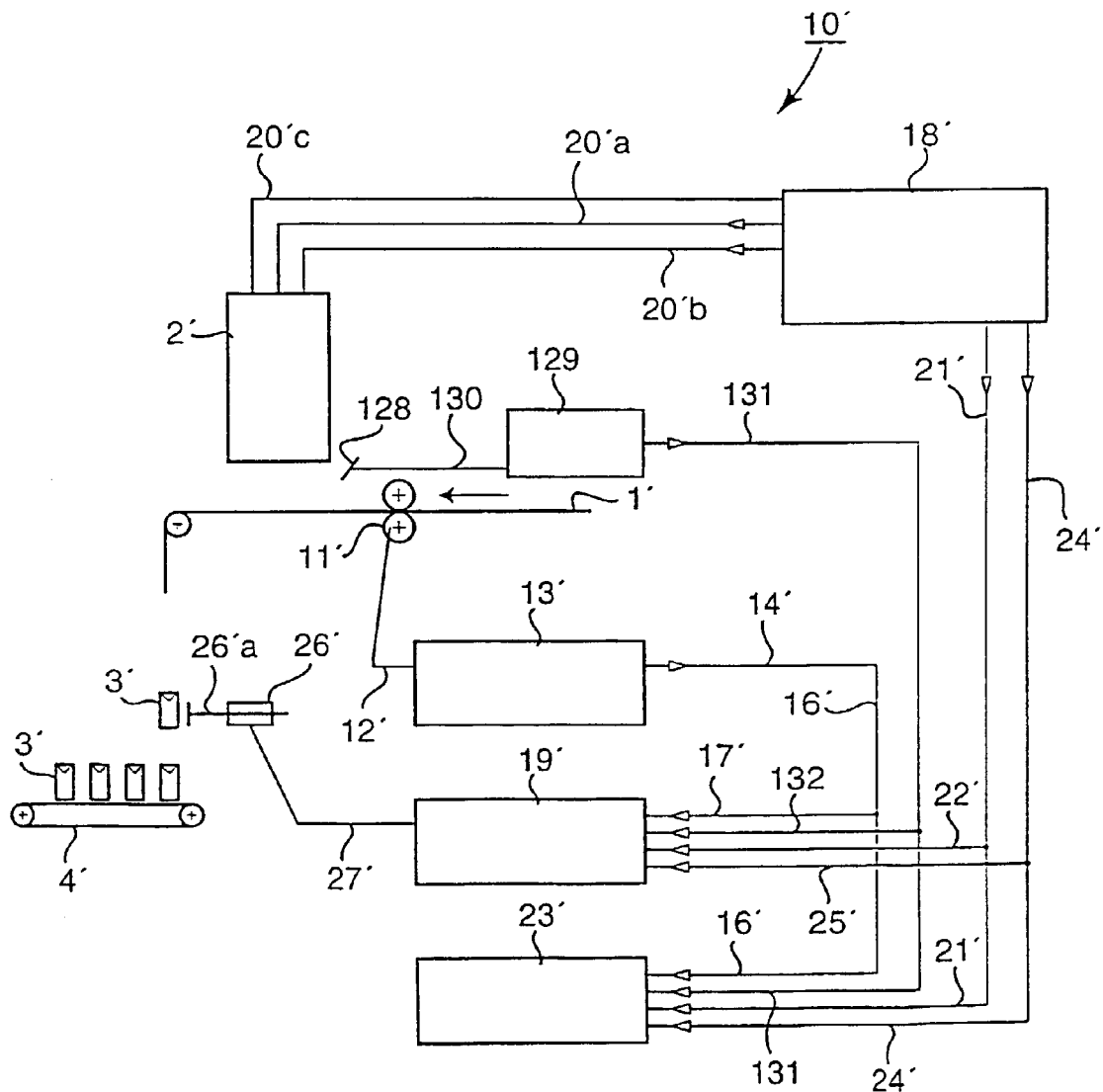

The present invention will now be described in greater detail hereinbelow, with particular reference to the accompanying Drawings. In the accompanying Drawings:

FIG. 1 is a schematic block diagram which shows a system for monitoring and control according to a first embodiment of the present invention in connection with the electron sterilisation of a packaging material web; and FIG. 2 is a schematic block diagram which shows a system for monitoring and control according to a second embodiment of the present invention in the electron sterilisation of a packaging material web.

It should be observed that, while the description with reference to the accompanying Drawings particularly refers to the sterilisation of a packaging material web as example of an object which is to be electron sterilised, the present invention is not restricted exclusively to this particular application. The present invention may be employed in the sterilisation also of other types and forms of objects, such as, for example, individual sheet-shaped packaging blanks, open, ready-to-fill packages etc. The expression "object" as employed here and in the appended claims is thus intended to encompass any type and form of object which is suitable for a continuous electron sterilisation.

DESCRIPTION OF PREFERRED EMBODIMENTS

FIG. 1 thus shows a simplified block diagram of a system according to a first embodiment of the present invention, carrying the generic reference numeral 10, in the sterilisation of a web 1 of a packaging material which, for the purpose of sterilisation, is irradiated with electrons from an electron radiation source 2 past which the web 1 is led or conveyed at a predetermined web speed in order, on its surface, to receive a sufficient electron dose for the desired sterilisation effect.

From the electron radiation source 2, the web 1 is led further to a forming and filling station (not shown) where the electron-sterilised web 1 is formed into packages which are filled with optional sterilised product and sealed to make finished packages 3 for further transport on a conveyor belt 4.

In the illustrated example, both the sterilisation of the web 1 and the forming, filling and sealing of the finished packages 3 take place with the aid of an aseptic packing and filling machine of the type which both sterilises, forms, fills and seals finished packages from a reel of the web-shaped packaging material magazined at the infeed end of the machine.

The system 10 for continuous monitoring and control of the electron sterilisation has a detector 11 placed at the electron radiation source 2 for sensing the pertinent web speed of the web 1 and in response the sensed web speed generating an electric signal which, via a conductor 12, is transmitted to a speed/voltage converter 13 which has an input in communication with the conductor 12.

The speed/voltage converter 13 converts the received electric signal into a process control signal which, in the current example, is a control signal calibrated with a norm value for filament current as the output signal. This output signal is transmitted via the conductor 14 and conductors 16 and 17 to a process control unit 19 which has a first input in communication with the conductor 17, and partly via the conductor 16 to a logging unit 23 which has a first input in communication with the conductor 16.

From a set norm value signal for filament current, the high voltage/filament current generator 18 generates an electric high voltage at a first output and an electric filament current at a second output, as well as an electric output signal proportional to the high voltage level at a third output and an electric output signal proportional to the filament current level at a fourth output.

The electric high voltage is transmitted via an electric cable 20a to the electron radiation source 2 which has a first input in communication with the cable 20a, and the electric filament current is transmitted via an electric cable 20b to the electron radiation source 2 which has a second input in communication with the cable 20b. Between the generator 18 and the electron radiation source 2, there is also disposed a zero conductor 20c.

The electric output signal for pertinent high voltage level is transmitted, on the one hand, via conductors 21 and 22 to the process control unit 19 which has a second input in communication with the conductor 22, and, on the other hand, via the conductor 21 to the logging unit 23 which has a second input in communication with the conductor 21.

The electric output signal for pertinent filament current is transmitted, on the one hand, via conductors 24 and 25 to the process control unit 19 which has a third input in communication with the conductor 25, and, on the other hand, via the conductor 24 to the logging unit 23 which has a third input in communication with the conductor 24.

On receipt of the output signals from the high voltage/filament current generator 18, the process control unit 19 compares these with corresponding, already input programmed norm values and generates, from these comparisons, either a positive electric comparison signal when these correspond to the predetermined norm values, or a negative electric comparison signal when the received signals from the high voltage/filament current generator 18 deviate prohibitively from the predetermined norm values.

The generated electric comparison signals are transmitted via a conductor 27 to an actuable ejector mechanism 26 with an ejector arm 26a at the discharge end of the packing and filling machine.

On receipt of a negative electric comparison signal, the ejector mechanism 26 activates the reciprocating ejector arm 26a for ejecting a discharged package 3, and on receipt of a positive electric comparison signal, the ejector mechanism 26 remains inactive and the ejector arm 26a thereby remains stationary so that discharged packages 3 may pass the ejector arm 26a unimpeded and be collected on the conveyor belt 4 for further transport and handling.

In the example above, it is assumed that the aseptic packing and filling machine is set to produce approximately 7,000 aseptic packages per hour, which corresponds to a web speed of approximately 0.6 m/s. It is further assumed that the electron radiation source 2 has a window directed towards the web 1 and that the distance between the web 1 and the window is set at approximately 12 mm.

On these assumptions, it is known that a satisfactory sterilisation effect will be obtained if the electron irradiation dose received by the web 1 on passage past the window of the electron radiation source 2 may be between 5 and 50 kGy, typically 25 kGy, and under the given assumptions, this dose will be achieved as long as the electron radiation source is supplied with a high voltage level between 40 and 90 kV, e.g. 75 kV, and a filament current level at, for example, 2.5 A depending upon the desired electron radiation dose. Should, for some reason, the high voltage level and/or the filament current level temporarily or permanently fall to values below these levels, the received electron radiation dose will be less and can be lower than 25 kGy, with the result that the web 1 will be insufficiently sterilised and that the produced packages will consequently be unusable.

If the speed of the web 1 were, for some reason, to be reduced and be lower than the set web speed, this entails (on condition that the remaining parameters are maintained according to the assumption above) that the web will receive an unnecessarily large electron radiation dose, with excessive sterilisation as a consequence. Should, on the other hand, the speed of the web 1 temporarily increase and be greater than the set web speed, the web will receive far too slight an electron irradiation dose and will be insufficiently sterilised, with unusable packages as a result, as long as the electron irradiation dose of the web is less than 25 kGy.

With the system in FIG. 2, the sterilisation process in FIG. 1 is monitored and controlled in such a manner that the electron irradiation dose received by the web 1 is constantly maintained at at least 25 kGy, at the same time as packages 3 are immediately ejected by means of the ejector mechanism 26 if the electron irradiation dose were, for some reason, to fall below 25 kGy.

As was described previously, the detector 11 continuously senses the speed of the web 1 at the electron radiation source 2 and generates, in response to the sensed speed, an output signal which is transmitted to the speed/voltage converter 13. The speed/voltage converter 13 receives the signal and converts it into an electric norm value signal for filament current which is transmitted, on the one hand, to the high voltage/filament current generator 18 and, on the other hand, to the process control unit 19. If the received, set norm value signal at the high voltage/filament current generator 18 is lower than the filament current signal which, on the occasion of sensing by the detector, is transmitted to the electron radiation source, the high voltage/filament current generator 18 generates, at its second output, an electric filament current signal for reducing the pertinent filament current to the electron radiation source for the immediate adjustment of the filament current to the correct level in view of the sensed web speed. At the same time, the process control unit 19 generates a negative electric output signal which is immediately transmitted to and activates the ejector mechanism 26 for ejecting the package(s) sterilised at the sensed, incorrect web speed.

If the set norm value signal at the high voltage/filament current generator 18 is higher than the filament current signal which, on the occasion of sensing by the detector, is transmitted to the electron radiation source, the high voltage/filament current generator 18 generates, at its second output, an electric filament current signal for increasing the pertinent filament current to the electron radiation source for the immediate adjustment of the filament current to the correct, higher level in view of the sensed web speed. At the same time, the process control unit 19 generates a negative electric output signal for transmission to and activation of the ejector mechanism 26, as previously.

If the set norm value signal at the high voltage/filament current generator 18 corresponds to the filament current signal which, on the occasion of sensing by the detector, is transmitted to the electron radiation source, the high voltage/filament current generator continues to transmit the same filament current signal to the electron radiation source as before. At this norm value signal, the process control unit 19 generates a positive electric output signal for transmission to the ejector mechanism 26 which, thus is not activated, but allows the packages to freely pass the ejector arm 26*a*.

All relevant real time parameter signals for monitoring and control of the sterilisation process are registered and stored continuously in the logging unit 23 throughout the entire sterilisation cycle.

In the illustrated system in FIG. 1, the process control unit 19 may preferably also be pre-programmed to generate a stop signal for stopping the web 1 and discontinuing the process entirely in such cases where, for example, the generator 18 twice or more in succession generates correction signals for filament current and/or high voltage to the electron radiation source 2. This may occur, for example, when the relevant high voltage level, because of operational disruptions in the outer mains power supply suddenly, but not just briefly, falls below a predetermined minimum level or to zero.

FIG. 2 shows a schematic block diagram of a system according to a second embodiment of the present invention which differs from the illustrated system in FIG. 1 principally in that it also includes one or more detectors (not shown) disposed at the electron radiation source 2 in communication with an amplifier 129 for detecting the electron irradiation dose emitted from the electron radiation source. Since the system in FIG. 2 otherwise includes substantially the same components as the system according to the first embodiment, the same or similar components have been given the same reference numerals as in FIG. 1 for purposes of clarity, but with the addition of a prima (') symbol.

The amplifier 129 receives and amplifies an electric output signal generated by the detector or the electron dosimeter 128 in response to the detected electron dose and generates an output signal which is transmitted, on the one hand, via conductors 131 and 132 to the process control unit 19' which has a fourth input in communication with the conductor 132 and, on the other hand, to the logging unit 23' which has a fourth input in communication with the conductor 131.

On the same assumptions in the description above of the system in FIG. 1 concerning the set web speed (e.g. 0.6 m/s) and distance (e.g. 12 mm) between the electron radiation source 2' and the web 1', it will be assumed also in this case that sufficient sterilisation effect is obtained at an electron irradiation dose of at least 25 kGy corresponding to a high voltage level of 75 kV and a filament current level of 2.5 A for the electron radiation source 2'.

If the speed of the web 1' should, for some reason, increase and be higher than the assumed web speed, i.e. 0.6 m/S, this entails that the web 1' receives a far too slight electron irradiation dose and consequently will be insufficiently sterilised as long as the received electron irradiation dose of the web is less than 25 kGy.

With the system in FIG. 2, the sterilisation process is monitored and controlled in the same manner as in the example in FIG. 1 in such a manner that the received electron irradiation dose throughout the entire sterilisation process is maintained at at least 25 kGy, at the same time as packages 3' are immediately ejected by means of the ejector mechanism 26' if the electron irradiation dose were, for some reason, to fall below 25 kGy.

As was described earlier, the detector 11' continuously senses the speed of the web 1' at the electron radiation source 2' and generates, in response to the sensed speed, an output signal which is transmitted to the speed/voltage converter 13'. The speed/voltage converter 13' receives the signal and converts it into an electric norm value signal for filament current which is transmitted, on the one hand, to the high voltage/filament current generator 18' and, on the other hand, to the process control unit 19'.

If the set norm value signal at the high voltage/filament current generator 18' is lower than the filament current signal which, on the occasion of sensing by the detector, is transmitted to the electron radiation source, the high voltage/filament current generator 18' generates, at its second output, an electric filament current signal for reducing the pertinent filament current to the electron radiation source for the immediate adjustment of the filament current to the correct level in view of the sensed web speed. At the same time, the process control unit 19' generates a negative electric output signal which is immediately transmitted to and activates the ejector mechanism 26' for ejecting the package(s) sterilised at the sensed, incorrect web speed.

If the set norm value signal at the high voltage/filament current generator 18' is higher than the filament current signal which, on the occasion of sensing by the detector, is transmitted to the electron radiation source, the high voltage/filament current generator 18' generates, at its second output, an electric filament current signal for increasing the pertinent filament current to the electron radiation source for the immediate adjustment of the filament current to the correct, higher level in view of the sensed web speed. At the same time, the process control unit 19' generates a negative electric output signal for transmission to and activation of the ejector mechanism 26', as previously.

If the set norm value signal at the high voltage/filament current generator 18' corresponds to the filament current signal which, on the occasion of sensing by the detector, is transmitted to the electron radiation source, the high voltage/filament current generator continues to transmit the same filament current signal to the electron radiation source as before. At this norm value signal, the process control unit 19' generates a positive electric output signal for transmission to the ejector mechanism 26' which, thus is not activated, but allows the packages 3' to freely pass the ejector arm 26'*a*.

With the aid of the detector or the electron irradiation dosimeter 128, the system in FIG. 2 can, unlike the system in FIG. 1, also monitor and control the process by detecting and output parameter, i.e. the electron irradiation dose from the electron radiation source 2' and thus not only by detecting an input parameter, such as web speed, which further increases the reliability of the system in continuous monitoring and control of the sterilisation. Should, in this example, the instantaneously detected electron irradiation dose fall below the predetermined requisite value, i.e. 25 kGy, the process control unit 19' will, on receipt of the output signal from the amplifier 129, immediately activate the ejector mechanism 26' for ejecting packages 3' which have been insufficiently sterilised because of the far too low electron irradiation dose at the relevant occasion of detection.

Thus, it will be apparent from the foregoing description that the present invention provides a system for monitoring and control which effectively and simply obviates the previously considered shortcomings and drawbacks in connection with the conventional sterilisation methods. In particular, the present invention realises a system by means of which electron sterilisation of a sheet- or web-shaped, or otherwise configured packaging blank may be continuously monitored and controlled throughout the entire sterilisation process in such a manner that an incorrectly sterilised packaging blank, or packages produced from the incorrectly sterilised packaging blank, may be immediately ejected without the sterilisation process needing to be discontinued as a result of the incorrect sterilisation. It will be obvious to a person skilled in the art that alterations and modifications in the two described embodiments may be put into effect without departing from the inventive concept as this is defined by means of the appended claims. Thus, the appended claims are intended also to encompass such alterations and modifications as are obvious to a person skilled in the art.

What is claimed is:

1. A system for monitoring and control in the sterilization of an object which, for the purpose of sterilization, is electron irradiated from an electron radiation source past which the object is led or conveyed in order to receive a sufficient irradiation dose for the intended sterilization effect, wherein it includes:

A detector for sensing the current speed of the object at the electron radiation source and generating an electric output signal which corresponds to the sensed speed;

A speed/voltage converter which has an input in communication with the detector for receiving the output signal from the detector and generating a control signal proportional to a norm value for filament current to the electron radiation source as a response thereto;

A high voltage/filament current generator which has an input for receiving a set norm value signal and, for generating in response thereto a high voltage at a first output in communication with the electron radiation source, a filament current at a second output in communication with the electron radiation source, an output signal for pertinent high voltage at a third output, and an output signal for pertinent filament current at a fourth output;

A process control unit which has a first input in communication with the converter for receiving the control signal from the converter, a second input in communication with the third output at the generator for receiving the generated output signal for pertinent high voltage, a third input in communication with the fourth output at the generator for receiving the generated output signal for pertinent filament current, said process control unit being disposed to compare the received electric signals with corresponding norm values pre-programmed in the process control unit and generating a positive electric comparison signal when the received signals correspond to the pre-programmed norm values, and a negative comparison signal when the received signals deviate prohibitively from the pre-programmed norm values in the comparison;

An ejector mechanism at or downstream of the electron radiation source in communication with the process control unit, for receiving the generated comparison signal from the process control unit, said ejector mechanism being disposed to be activated for ejecting the sterilized objects when the received comparison signal is negative, and to be inactivated when the received comparison signal is positive.

2. The system as claimed in claim 1, wherein the system also includes a logging unit which has a first input in communication with the converter for receiving and storing the norm value signal from the converter, a second input in communication with the third output at the generator for receiving and storing the output signal for pertinent high voltage and a third input in communication with the fourth output at the generator for receiving and storing the output signal for pertinent filament current.

3. The system as claimed in claim 1, wherein the system has a dosimeter at the electron radiation source for continuous measurement of the relevant electron irradiation dose from the electron radiation source and for generating, in response to the relevant electron irradiation dose, an electric signal for transmission to the process control unit which has a fourth input in communication with the dosimeter.

4. The system as claimed in claim 3, wherein the dosimeter is also in communication with the logging unit which has a fourth input in communication with the dosimeter.

5. The system as claimed in claim 3, wherein the process control unit is disposed to generate a positive electric comparison signal when the received output signal from the dosimeter corresponds with a norm value pre-programmed in the process control unit for electron irradiation dose, and a negative comparison signal when the received output signal from the dosimeter deviates prohibitively from the pre-programmed norm value for electron irradiation dose.

6. The system as claimed in claim 3, wherein the dosimeter is disposed to transmit the output signal to the process control unit and the logging unit, respectively, via an amplifier.

7. The system as claimed in claim 1, wherein the object which is to be sterilized is a sheet- or web-shaped packaging blank for aseptic packages.

8. The system as claimed in claim 1, wherein the object which is to be sterilized is a ready-to-fill package.

* * * * *